(12) United States Patent
Wiederin et al.

(10) Patent No.: US 6,864,974 B1
(45) Date of Patent: Mar. 8, 2005

(54) SYSTEM FOR USE IN CONDITIONING A SAMPLE FOR INTRODUCTION INTO A SAMPLE ANALYSIS SYSTEM

(75) Inventors: Daniel R. Wiederin, Omaha, NE (US); Gary J. Barrett, Omaha, NE (US)

(73) Assignee: Elemental Scientific Inc., Omaha, NE (US)

( * ) Notice: Subject to any disclaimer, the term of this patent is extended or adjusted under 35 U.S.C. 154(b) by 160 days.

(21) Appl. No.: 10/384,880

(22) Filed: Mar. 7, 2003

(51) Int. Cl.[7] .......................... G01N 21/73; G01N 1/00
(52) U.S. Cl. .................... 356/316; 356/36; 250/288
(58) Field of Search .................. 356/36, 315, 316; 250/288

(56) References Cited

U.S. PATENT DOCUMENTS 3,438,711 A * 4/1969 Hell ........................... 356/36
5,033,541 A * 7/1991 D'Silva ...................... 165/114
5,534,998 A * 7/1996 Eastgate et al. ............ 356/316
2003/0213907 A1 * 11/2003 Rutzke et al. .............. 250/288

* cited by examiner

Primary Examiner—F. L. Evans
(74) Attorney, Agent, or Firm—Thomte, Mazour & Niebergall; Dennis L. Thomte (57) ABSTRACT

A sample introduction system for ICPMS and ICPAES comprising a nebulizer which sprays liquid samples into a heated cyclonic spray chamber which has a common exit port for both liquid waste and sample aerosol which is coupled to a desolvation system comprised of condenser and revaporization loops that alternately condense solvent vapor both on the inner walls of the loop and in the aerosol stream, then revaporize the portion of solvent condensed in the aerosol stream for subsequent condensation in the next loop. The exit port of the system is capable of being directly or remotely coupled to the ICP injector tube.

31 Claims, 9 Drawing Sheets

SYSTEM FOR USE IN CONDITIONING A SAMPLE FOR INTRODUCTION INTO A SAMPLE ANALYSIS SYSTEM

BACKGROUND OF THE INVENTION

1. Field of the Invention

This invention relates to system for conditioning a sample for introduction into a sample analysis system and more particularly a system which conditions a sample for introduction into a sample analysis system such as an Inductively Coupled Plasma Mass Spectrometer (ICP-MS) or an Inductively Coupled Plasma Atomic Emission Spectrometer (ICP-AES).

2. Description of the Prior Art

Inductively Coupled Plasma Mass Spectrometry (ICP-MS) and Inductively Coupled Plasma Atomic Emission Spectrometry (ICP-AES) are two common analytical techniques used by laboratories for the determination of trace element concentrations in liquid samples. The ICP is an electromagnetically generated partially ionized argon plasma which a temperature of approximately 7000K. When a sample is introduced to the ICP, the high temperature causes sample atoms to become ionized or emit light. Since each chemical element produces a characteristic mass or emission spectrum, measuring said spectra allows the determination of the elemental composition of the original sample.

In normal operation, a liquid sample must first be dispersed into an aerosol prior to measurement using an ICPMS or ICPAES instrument. Typically, a polydisperse aerosol is created utilizing a nebulizer. The aerosol is then sorted in a spray chamber to remove the larger aerosol particles. Other processes such as aerosol agglomeration which causes larger droplets to form from smaller ones may also occur inside the spray chamber. Upon leaving the spray chamber, the aerosol is introduced to the ICPMS or ICPAES via a tubular injector. Transport efficiency of the nebulized sample out of the spray chamber may typically range from only 20% down to 2%, depending upon the type of nebulizer employed, the quality of aerosol produced by the nebulizer, and the sample liquid flow rate. This means that typically the majority of the sample goes to waste, reducing the potential intensity of the analytical signal.

SUMMARY OF THE INVENTION

A sample introduction system for ICPMS and ICPAES is disclosed which is comprised of a nebulizer which sprays liquid samples into a heated cyclonic spray chamber without the need of an additional gas port and which has a common exit port for both liquid waste and sample aerosol. The common exit port is coupled to a desolvation system which is comprised of substantially tubular-cross-section oval-shaped condenser and revaporization loops that alternately condense solvent vapor both on the inner walls of the loop and in the aerosol stream, then revaporize the portion of the solvent condensed in the aerosol stream for subsequent condensation in the next loop. When the desolvation system is made from a hydrophobic material resistant to hydrofluoric acid, the condenser loop is comprised of a hollow block member having curved internal surfaces to smoothly remove condensed solvent to waste. The exit port of the desolvation system is capable of being directly or remotely coupled to the ICP injector tube.

It is therefore a principal object of the invention to provide an improved sample introduction system for use in conjunction with a sample analysis system.

A further object of the invention is to provide a sample introduction system for ICPMS and ICPAES techniques.

Yet another object of the invention is to provide a high-density sample introduction system for ICP emission or mass spectrometry (ICPAES, ICPMS) which is comprised of a heated cyclonic spray chamber coupled to a multi-stage condenser system with a substantially tubular pathway.

Still another object of the invention is to provide a system of the type described wherein the multi-stage condenser is arranged in oval-shaped loops to improve surface contact and compact design.

Still another object of the invention is to provide a system of the type described wherein the exit port of the multi-stage condenser has a direct connection to the injector base of the ICPMS torch.

Still another object of the invention is to provide a system of the type described wherein the heated cyclonic spray chamber does not require an additional gas port.

Still another object of the invention is to provide a sample introduction system wherein the heated cyclonic spray chamber has an inside diameter of approximately 60 mm to 150 mm.

Yet another object of the invention is to provide a sample introduction system including a heated cyclonic spray chamber having a common exit port for both sample aerosol and liquid waste.

Yet another object of the invention is to provide a sample introduction system including a heated cyclonic spray chamber wherein the connections thereof are O-ring free.

Yet another object of the invention is to provide a high sensitivity sample introduction system including a heated cyclonic spray chamber which is resistant to hydrofluoric acid.

Still another object of the invention is to provide a sample introduction system including a heated cyclonic spray chamber wherein the temperature of the spray chamber wall is 10° C. to 100° C. higher than the boiling point of the solution being analyzed.

Yet another object of the invention is to provide a sample introduction system including a heated cyclonic spray chamber wherein the heating mechanism therefore is not electrically insulating.

Still another object of the invention is to provide a high sensitivity sample introduction system including a heated cyclonic spray chamber wherein the cyclonic spray chamber is heated by direct contact with an electrically conductive heating mechanism.

Yet another object of the invention is to provide a sample introduction system including a heated cyclonic spray chamber wherein a layer of heated fluid (gas or liquid) lies between the electrically conductive heating mechanism and the cyclonic spray chamber.

Still another object of the invention is to provide a high sensitivity sample introduction system including multiple-stage solvent condensers which repetitively heat and cool the aerosol stream in series wherein ambient temperature is used to revaporize the solvent aerosol.

Yet another object of the invention is to provide a multiple-stage solvent condenser for a sample introduction system wherein the number of condenser loops thereof is greater than three. Still another object of the invention is to provide a multiple-stage solvent condenser wherein the condenser material is constructed from material which is resistant to hydrofluoric acid.

Yet another object of the invention is to provide a sample introduction system wherein the multiple-stage solvent condensers thereof are constructed of hydrophobic materials resistant to hydrofluoric acid with an extended, elliptical, or channelized shape that prevents sample aerosol from impacting on a surface or being lost and causing analyte contained therein from being removed from the sample aerosol stream.

Still another object of the invention is to provide a condenser which is constructed from PFA material.

Yet another object of the invention is to provide a system of the type described above wherein the PFA condenser consists of a series of slots.

Yet another object of the invention is to provide a system of the type described which permits remote coupling of the sample aerosol.

These and other objects will be apparent to those skilled in the art.

DESCRIPTION OF THE PREFERRED EMBODIMENT

The system or apparatus of this invention for conditioning a liquid sample for introduction into a sample analysis system such as an Inductively Coupled Plasma Mass Spectrometer (ICP-MS) or an Inductively Coupled Plasma Atomic Emission Spectrometer (ICP-AES) is referred to generally in the drawings with the reference numeral 10. Apparatus 10 is a small, lightweight portable unit which preferably is contained within a housing 12 including a base 14, an upstanding front wall 16 having a grill 18, a selectively removable housing member 20 having grills 22 and 24 formed therein, and a selectively removable cover 26.

Figure 1:
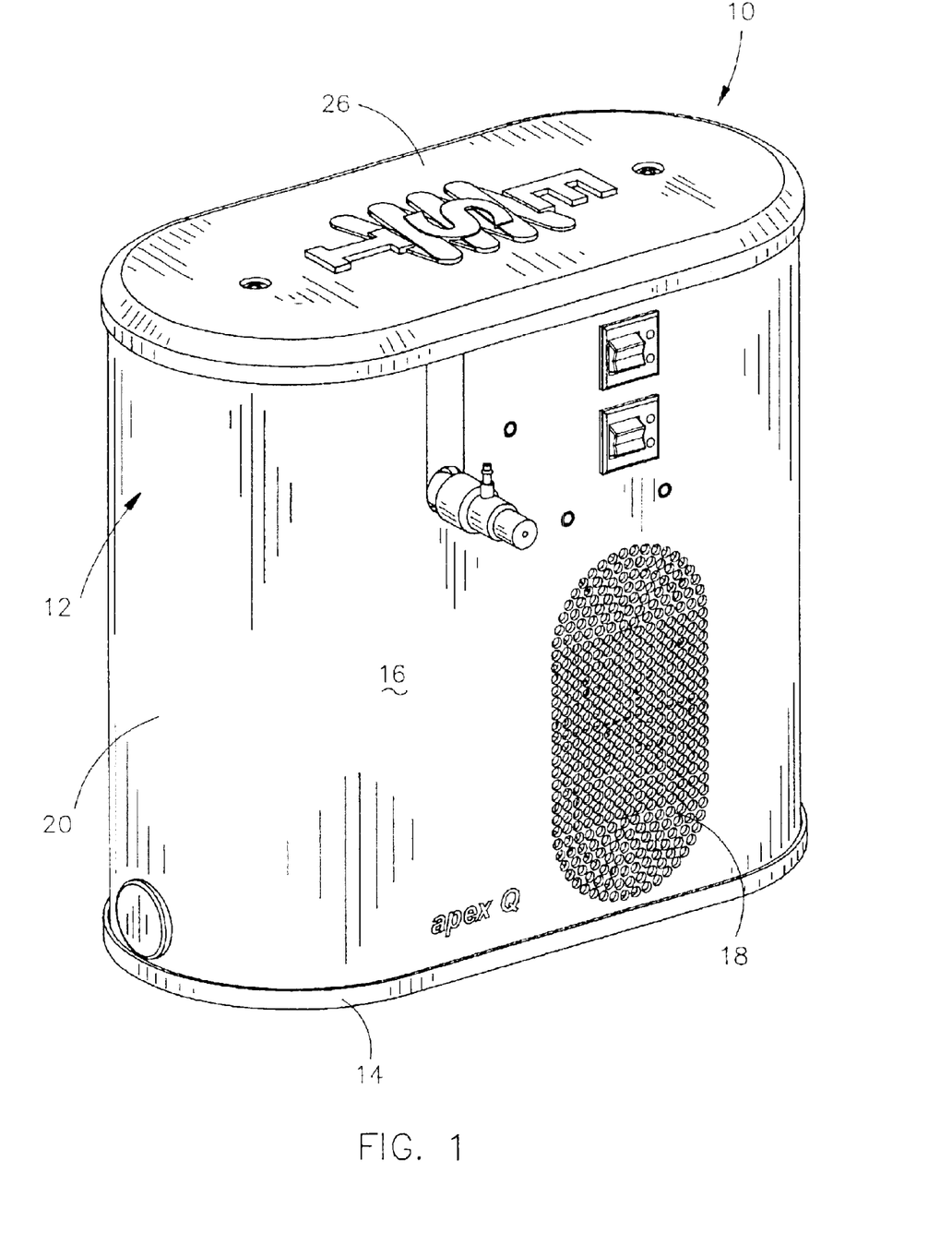
FIG. 1 is a front perspective view of the system or apparatus of this invention.
Figure 2:
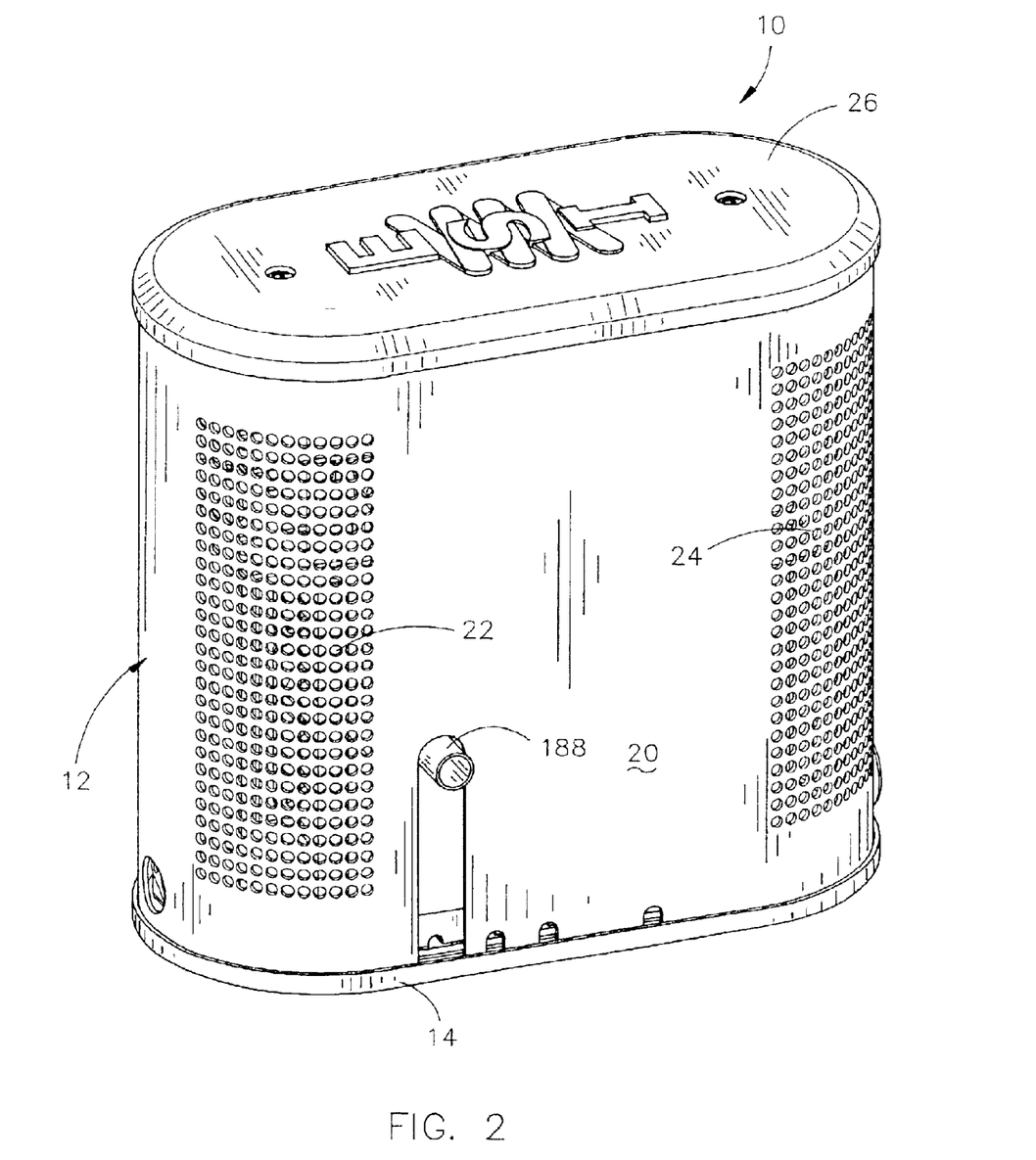
FIG. 2 is a rear perspective view of the system or apparatus of this invention.
Figure 3:
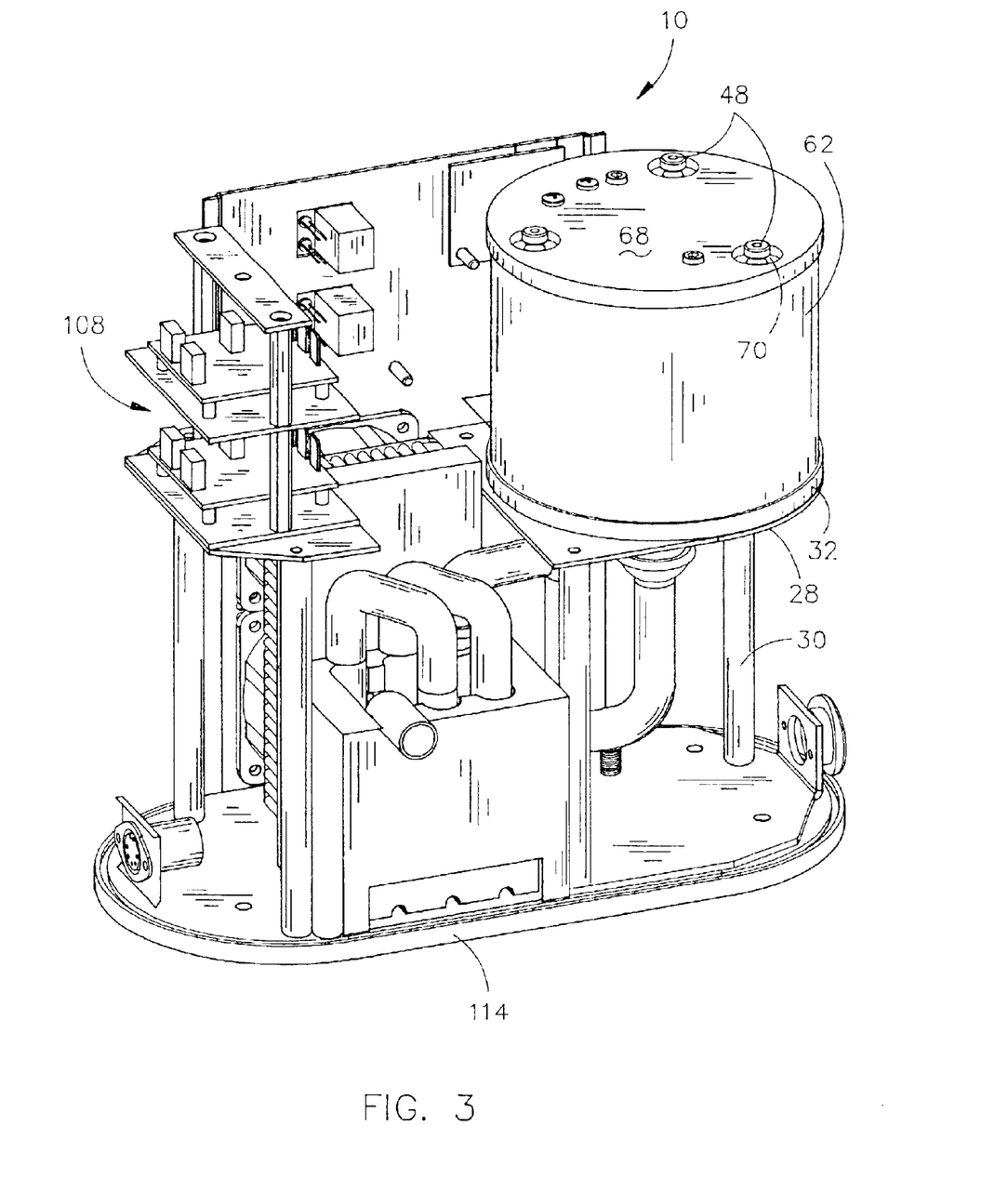
FIG. 3 is a rear perspective view of the system or apparatus of this invention with the housing thereof removed.

As seen in FIG. 3, support 28 is positioned within the housing 12 and is supported above base 14 by a plurality of posts 30. A plastic disc 32 is mounted on support 28. A plurality of screws extend upwardly through support 28 and disc 32 and have Teflon spacers 36 mounted thereon which are supported upon disc 32. The numeral 37 refers to an oven assembly including a cup-shaped, heat conductive lower oven member 38 mounted on the upper ends of the spacers 36 and includes a bottom wall 40 which has screws threadably received therein to securely mount the oven member 38 above the disc 32 and support 28. The upper inside surface of bottom wall 40 is tapered or conical-shaped and has an opening 42 formed therein which registers with openings formed in disc 32 and support 28. Oven member 38 also includes a cylindrical wall 44 extending upwardly from bottom wall 40 and which as a slot 46 formed therein. Threaded screws 48 extend upwardly from the upper end of cylindrical wall 44, as seen in the drawings. Oven member 38 is comprised of an electrically conductive metal material such as aluminum. Oven member 38 is resistively heated using an electronically controlled heating mechanism, such as one or more voltage cartridge heaters 49 that are inserted into the lower port of oven member 38. A temperature sensor, e.g., thermocouple device, is also inserted into the lower portion of the oven member 38 to measure and control the oven temperature via a feedback circuit.

Figure 4:
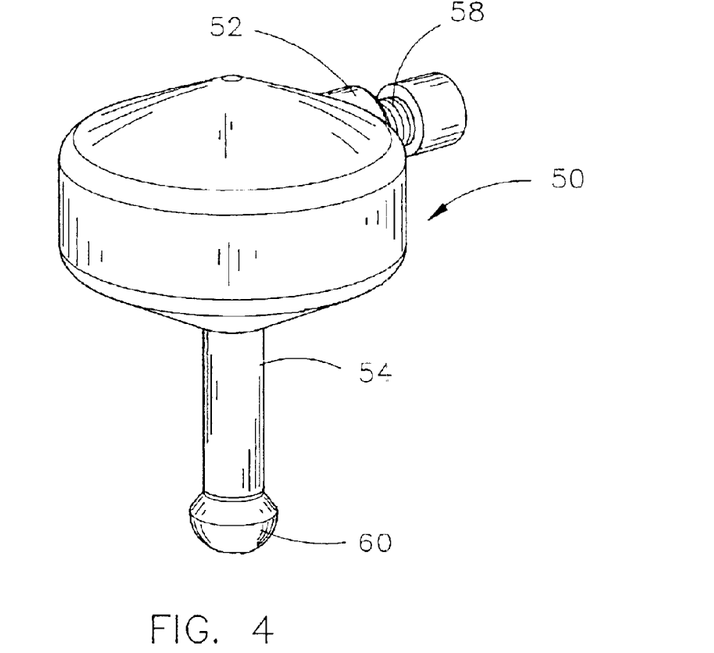
FIG. 4 is a perspective view of one embodiment of the cyclonic spray chamber of this invention.
Figure 5:
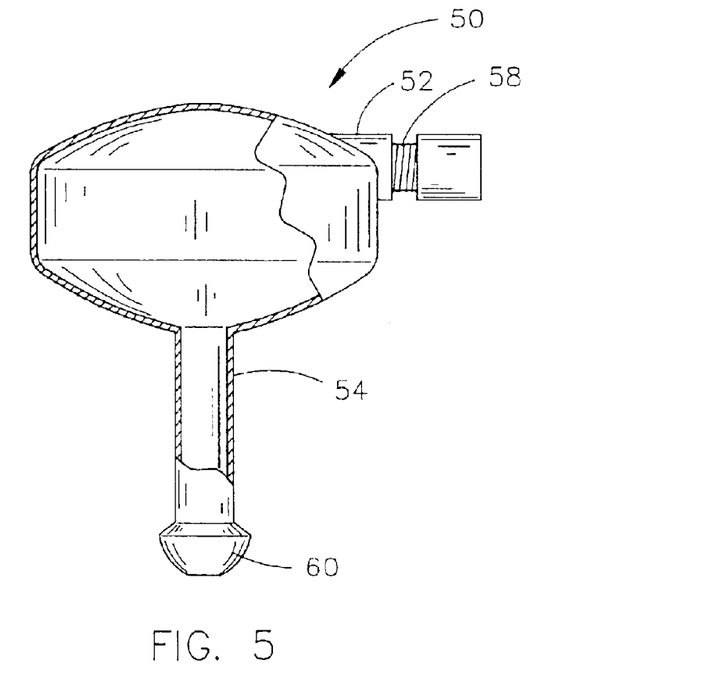
FIG. 5 is a side view of the cyclonic spray chamber of FIG. 4 with portions thereof cut away to more fully illustrate the same.

The numeral 50 refers to a hollow cyclonic spray chamber (first embodiment) having an inlet portion 52 and an outlet portion 54. Inlet portion 52 extends from spray chamber 50 outwardly through an opening 56 formed in front wall 16 and has a plastic, externally threaded connector 58 mounted thereon. A liquid sample for chemical analysis is delivered to the entrance port 190 on a pneumatic nebulizer 192, operatively connected to inlet portion 52 by connector 58, by venturi action or a pumping system. The nebulizer 192 converts the liquid sample into an aerosol by interaction of nebulizing gas introduced through a second port 194 on the nebulizer 192 with a narrow column of the liquid sample. The nebulizer aerosol is introduced to the cyclonic spray chamber through the off-axis inlet portion 52 so that a swirling or cyclonic motion of the aerosol within the spray chamber is created. Outlet portion 54 has a connector portion 60 mounted on its lower end.

Preferably, spray chamber 50 has an inside diameter between 60 mm and 150 mm which is greater than the typical 50 mm inside diameter of prior art cyclonic spray chambers. Surprisingly, by increasing the diameter of the cyclonic spray chamber, the sensitivity was increased. In the first embodiment of the invention, the cyclonic spray chamber is comprised of a glass material. The numeral 62 refers to a metal, cylindrical shield which has its lower end received in an annular groove formed in the upper surface of disc 32. Shield 62 has a U-shaped slot formed therein which receives the inlet portion 52 of spray chamber 50 extending therethrough. The shield or housing 62 is spaced approximately 0.25 inches outwardly of the oven assembly 37 comprised of oven members 38 and 76. The air gap between shield 62 and the oven assembly 37 serves to insulate the oven assembly 37 from the ambient environment while allowing the cyclonic spray chamber to be evenly heated to a controlled temperature between 10° C. to 100° C. above the boiling point of the liquid sample.

The numeral 66 generally refers to a cover assembly designed to close the upper end of member 38 and the upper end of shield 62. Cover assembly 66 includes a disc-shaped, plastic lid 68 having openings formed therein adapted to have the screws 48 extending upwardly therethrough. Nuts 70 are mounted on the screws 48 to hold the over assembly in place. An L-shaped bracket 72 is secured to the underside of lid 68 with the leg portion 74 thereof being received by the slot 64 in shield 62. The lower end of leg portion 74 is arcuate to correspond to the upper exterior surface of inlet portion 52 of spray chamber 50.

The numeral 76 refers to a disc-shaped upper oven member having a central opening 78 formed therein. The lower surface 77 of oven member 76 is tapered or conical-shaped so as to be compatible to the upper surface of spray chamber 50. The diameter of oven member 76 is very slightly less than the inside diameter of oven member 38 to permit oven member 76 to be received by oven member 38. A pair of spaced-apart studs 78–80 have their lower ends secured to oven member 76 and extend therefrom upwardly through counter-sunk openings formed therein. Studs 78–80 have head portions thereon which are larger than the shanks thereof to permit upward movement of studs 78–80 and oven member 76 relative to lid 68 while limiting the downward movement of studs 78–80 and oven member 76 with respect to lid 68. Springs 82 and 84 embrace studs 78 and 80, respectively, to yieldably urge oven member 76 downwardly with respect to lid 68. Thus, the conical-shaped lower surface 77 of oven member 76 yieldably engages the conical-shaped upper end of spray chamber 50. Oven member 76 is preferably constructed of an aluminum material identical to oven member 38.

The oven member 76 is close-fitted to oven member 38 to create a uniform heater. The spring mounting of oven member 76 ensures that the oven member 38 makes a good thermal contact with the top of the cyclonic spray chamber yet is flexible so that a cyclonic spray chamber made from glass or other fragile material will not be damaged.

Figure 6:
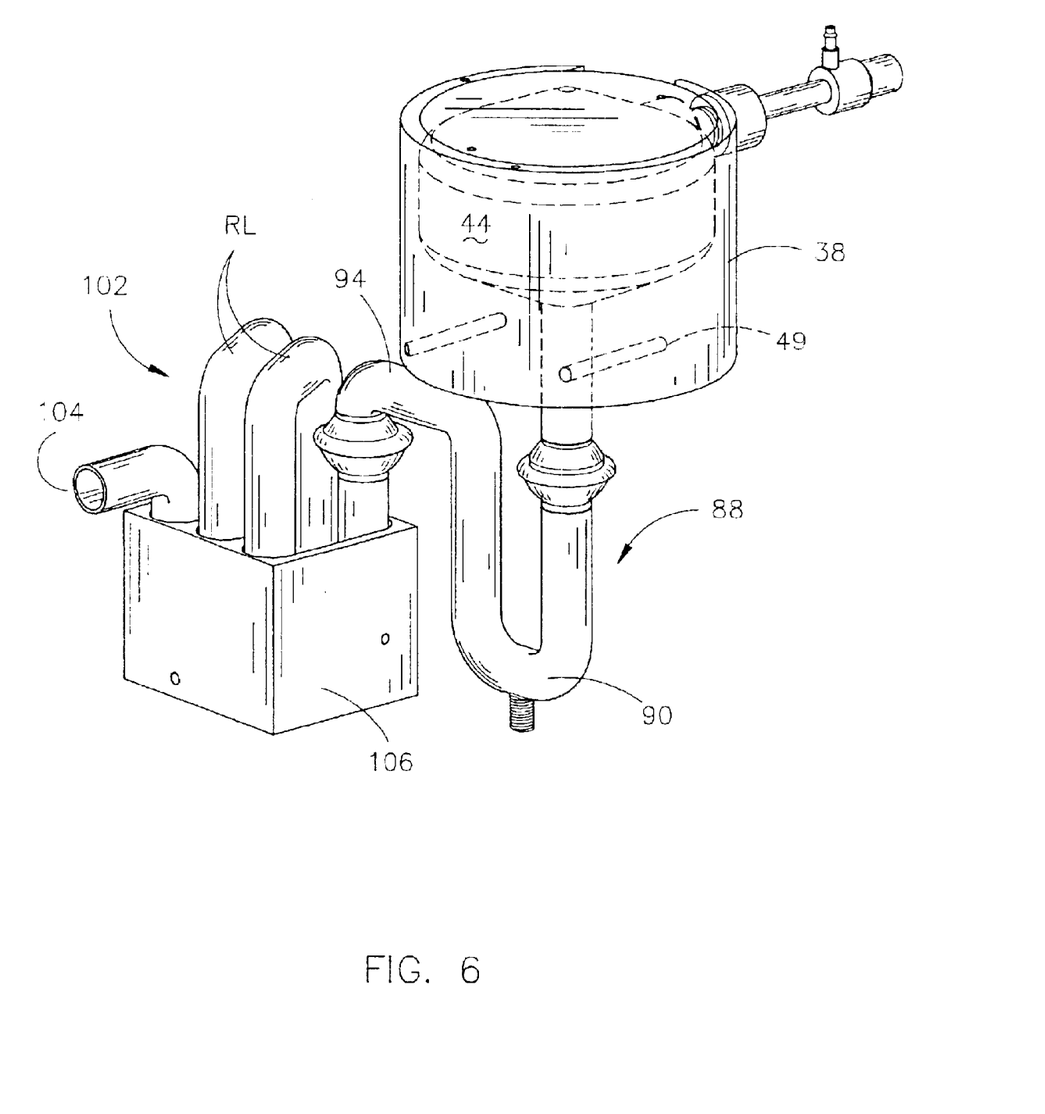
FIG. 6 is a partial perspective view of a portion of one embodiment of the invention.
Figure 7:
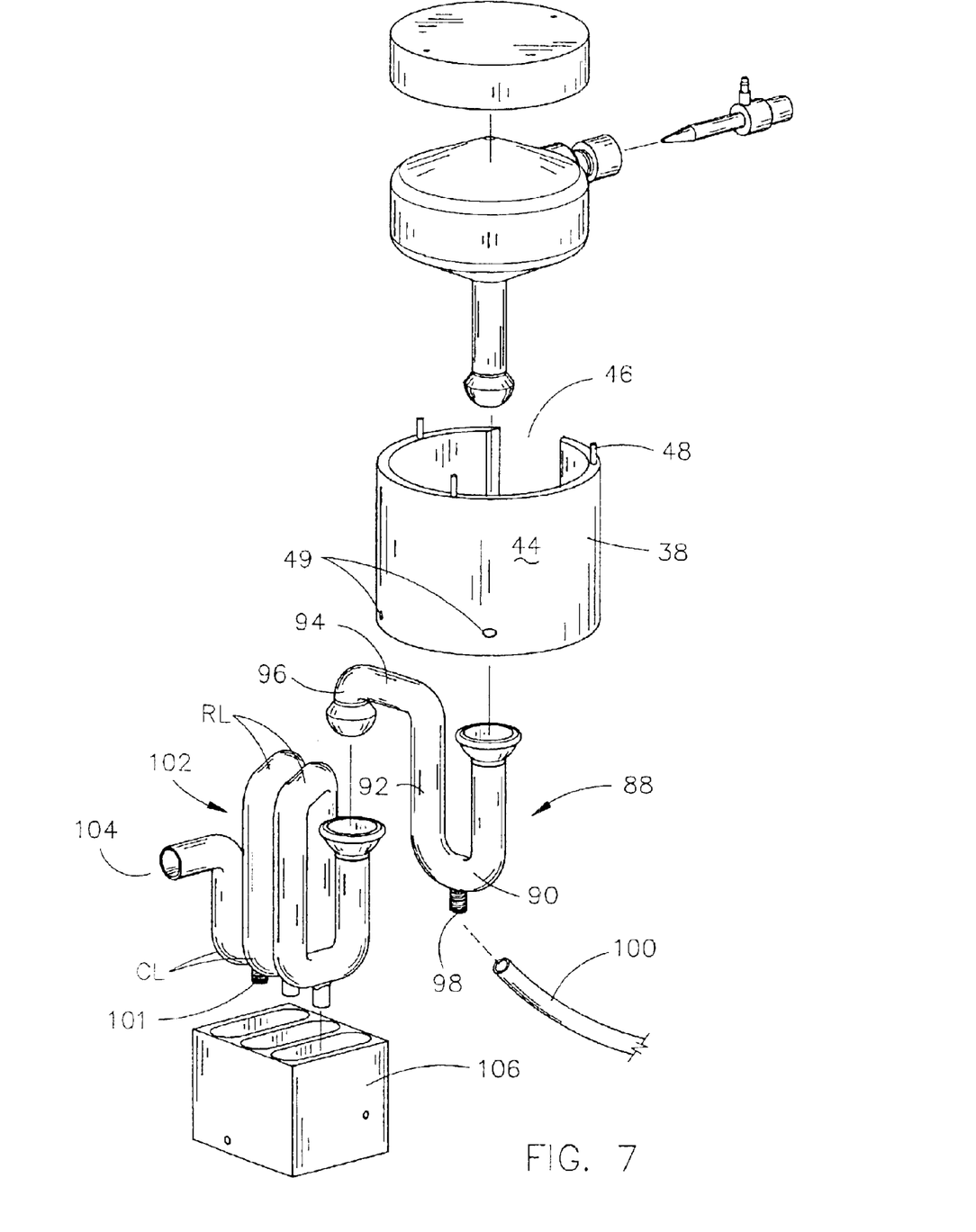
FIG. 7 is an exploded perspective view of the embodiment of FIG. 6.
Figure 8:
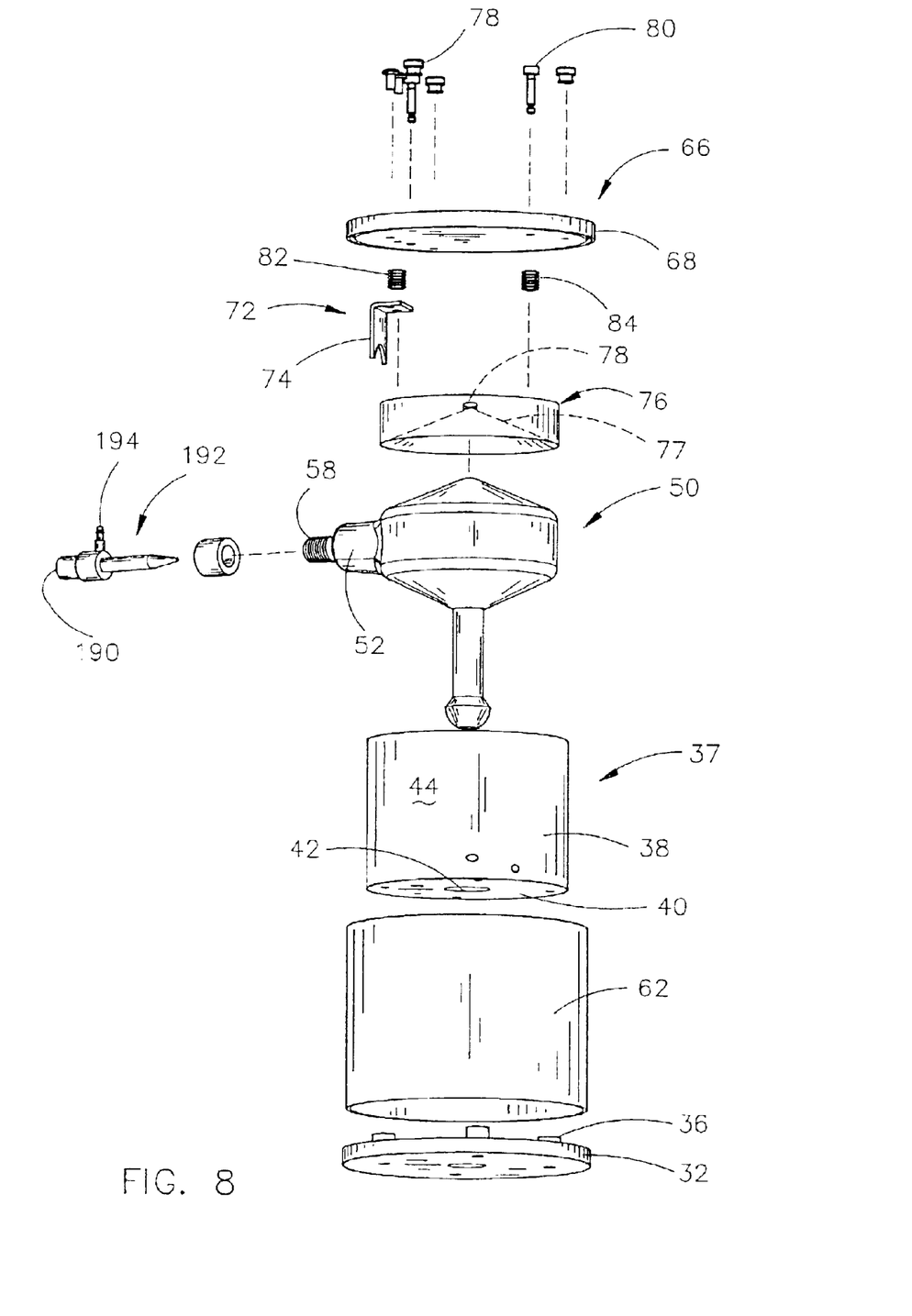
FIG. 8 is a partial exploded perspective view of the embodiment of FIG. 6.

The numeral 86 refers to a tubular member including tube portions 88, 90, 92, 94 and 96. The upper end of tube portion 88 is selectively removably connected to the connector element 60 on the lower end of outlet portion 54 of spray chamber 50 or by any other convenient means. Tube portions 88, 90 and 92 form a primary condenser loop. As seen in the drawings, tube portion 90 has a discharge port or nipple 98 extending therefrom to which a discharge hose or conduit 100 is affixed. A plurality of oval-shaped condenser and revaporization loops are in communication with tube portion 96. (FIG. 7). For purposes of description, the lower ends of the loops are condenser loops (CL) while the upper ends of the loops are revaporizing loops (RL). Each of the condenser loops CL has a discharge port or nipple 101 extending therefrom to which a discharge hose or conduit is affixed. The alternating condenser and revaporization loops will be referred to as a desolvation system 102. The discharge end 104 of the system 102 is preferably directly connected to the inlet of the ICP-MS or ICP-AES. As seen in the drawings, the condenser loops of the system 102 are enclosed within a conventional thermoelectric cooling device 106 such as sold by Tellurex Corporation. The revaporization loops RL are exposed to ambient temperatures within the housing. The numeral 108 refers generally to the control circuitry of the system.

Figure 9:
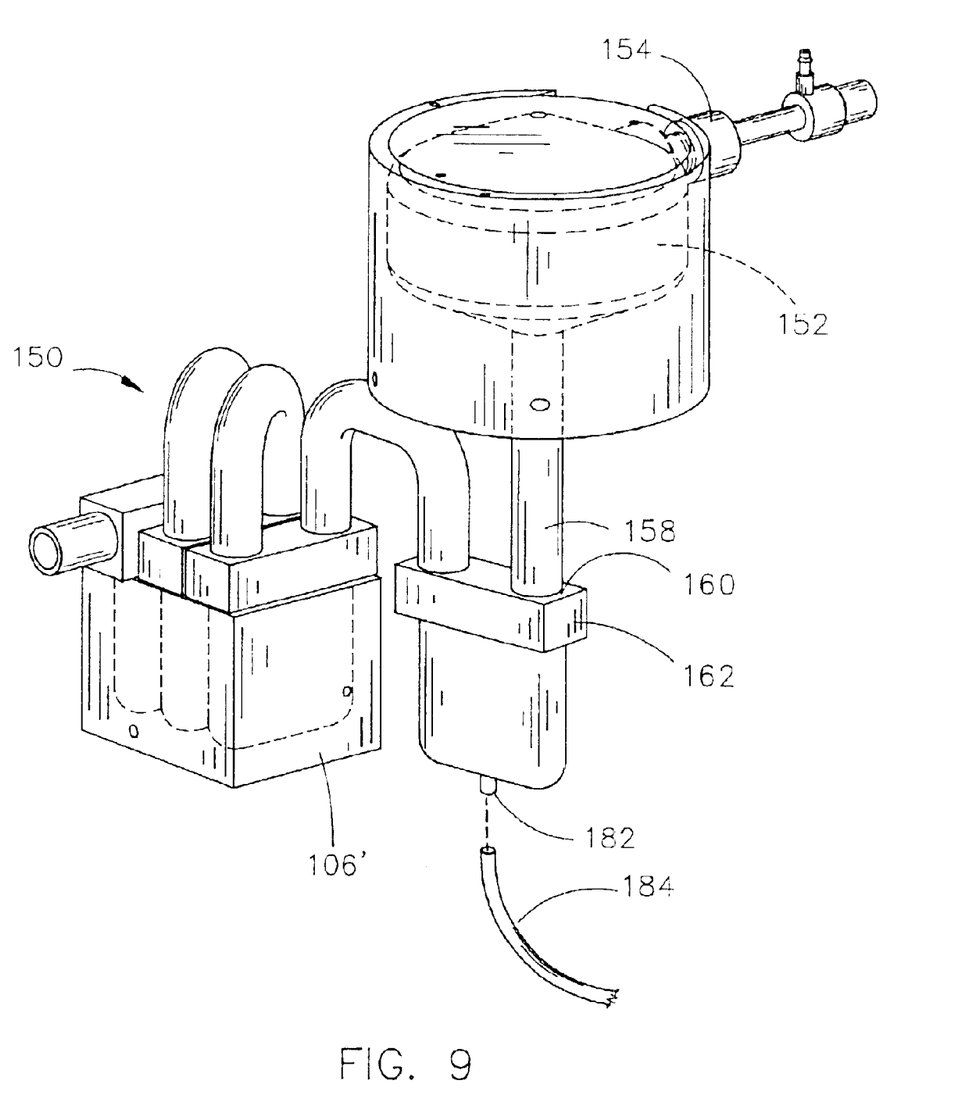
FIG. 9 is a perspective view of a modified form of a portion of the invention.
Figure 10:
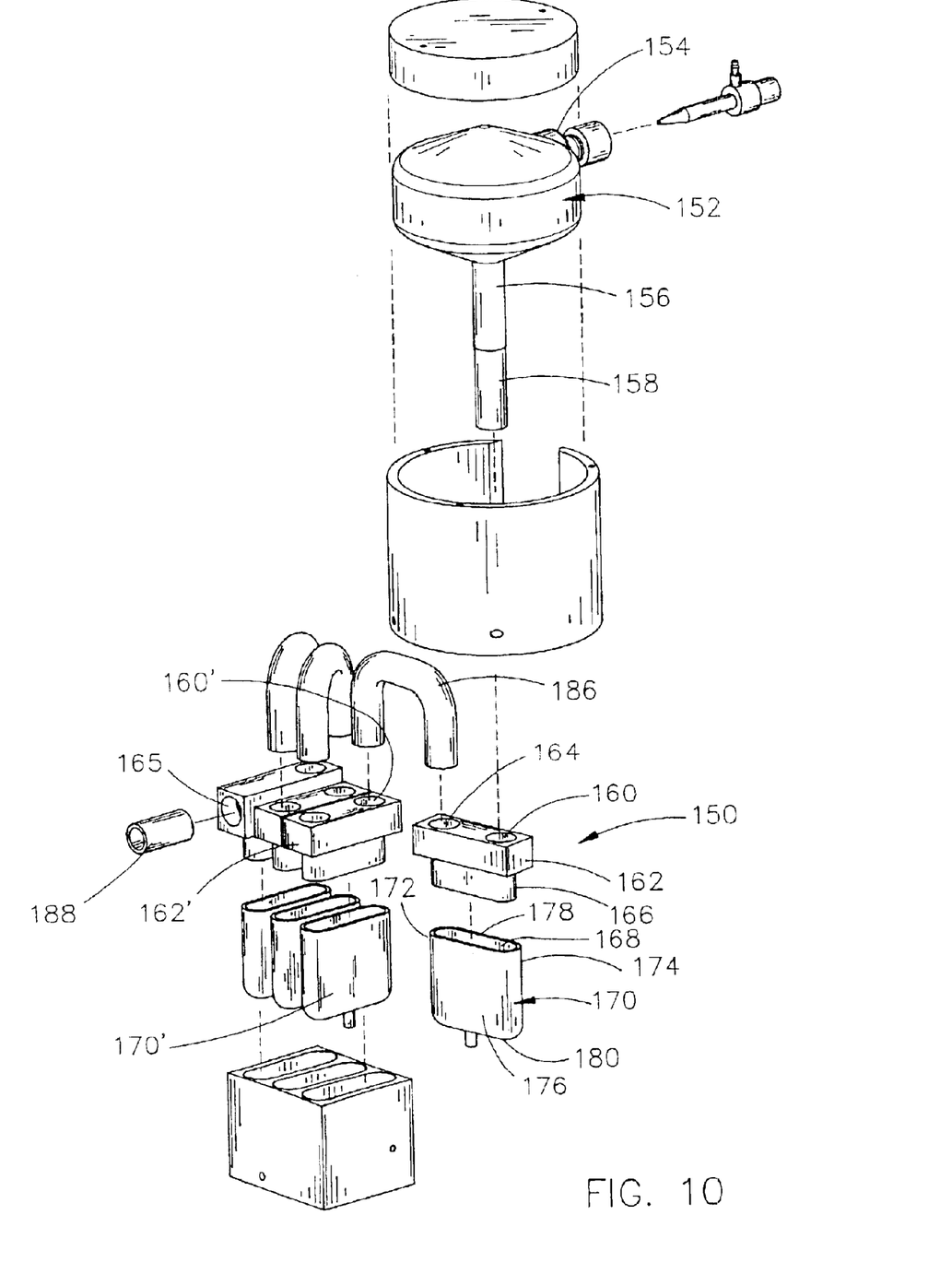
FIG. 10 is an exploded perspective view of the form of the invention of FIG. 9.

FIGS. 9 and 10 illustrate a second embodiment of the desolvation system of this invention which is designed with the reference numeral 150 and a second embodiment of the cyclonic spray chamber which is designated with the reference numeral 152. The primary difference between chamber 152 and the chamber 50 is that chamber 152 is constructed of a hydrophobic material resistant to hydrofluoric acid such as Teflon PFA while the chamber 50 is constructed of a glass material. A major difference between desolvation system 150 and desolvation system 102 is that system 150 is constructed of a hydrophobic material resistant to hydrofluoric acid such as Teflon PFA while system 102 is constructed of a glass material.

Referring to FIG. 9, the inlet portion 154 of chamber 152 has a reduced diameter portion at its outer end adapted to be placed in communication with a nebulizer or the like. The outlet portion 156 is adapted to have a tube 158 secured thereto which is removably received by an inlet opening 160 formed in cap 162. Cap 162 also has a discharge opening 164 formed therein. Cap 162 includes an elongated oval section 166 extending downwardly therefrom which is adapted to be received within the open upper end 168 of a hollow block member 170. Block member 170 includes end walls 172 and 174, side walls 176 and 178, and bottom wall 180 which has a discharge nipple or port 182 extending therefrom adapted to have a hose 184 or tubing secured thereto. As seen in the drawings, the openings 160 and 164 are positioned closely adjacent the semi-circular ends of oval section 166 so that those openings are positioned closely adjacent the end walls 172 and 174 of block member 170. The end walls 172 and 174 each have an arcuate or semi-circular cross section. Further, the bottom wall 180 has an arcuate or semi-circular cross section.

An inverted U-shaped tube 186 has one end received in discharge opening 164 of cap 162 and has its other end received within inlet opening 160' of cap 162' which is mounted on block member 170'. Any number of tubes 186, 186', etc., block members 170, 170', etc., may be employed. The tubes 186, 186', etc., function as revaporization loops while the block members 170, 170', etc., function as condensers. The condensers (block members) are enclosed in cooling apparatus or unit 106' which is substantially identical to unit 106 utilized in the first embodiment of the desolvation system.

The cap which is mounted on the last block member (condenser) has its discharge opening 165 extending out the end of the cap rather than the top of the cap so that the tube 188 mounted therein may be extended outwardly through the rearward side of housing member 20.

The operation of the sample introduction system of this invention is generally summarized as follows. A liquid sample for chemical analysis is delivered to the entrance port 190 on the pneumatic nebulizer 192 as described. Nebulizer 192 converts the liquid sample into an aerosol by interaction of nebulizing gas introduced through the port 194 on the nebulizer 192 with a narrow column of the liquid sample. The nebulized aerosol is introduced to the heated cyclonic spray chamber through the off-axis inlet portion 52 so that a swirling or cyclonic motion of the aerosol within the spray chamber is created. The oven assembly 37 of this invention and the construction of the oven assembly ensures that the walls of the spray chamber will have an even temperature which is preferably 10° C. to 100° C. above the boiling point of the liquid sample.

The heated walls of the spray chamber in both of the embodiments described above create a convection flow of expanding gas radiating away from the walls of the cyclonic spray chamber toward the inside of the chamber. The heat generated causes liquid solvent in the aerosol particles to evaporate leaving behind smaller partially dried or dried aerosol particles containing salts or other solid materials that were originally dissolved in the liquid sample. In cases where the volume of sample liquid introduced is relatively small, essentially all of the aerosol will be dried. The heated mixture of dried aerosol particles and solvent vapor, along with liquid waste, if any, is carried out of the spray chamber through the single exit port 54 of cyclonic spray chamber 50 or the outlet 156 of the cyclonic spray chamber 152 located at the bottom of the chamber. If the spray chamber is not heated, then the majority of the liquid aerosol particles will impact the walls of the chamber to coalesce and flow to a drain as waste, substantially reducing the signal at the ICP instrument.

The exit of the cyclonic spray chamber leads out of the heated oven enclosure and is attached to a primary condenser which is substantially tubular in form when constructed of hydrophilic material such as quartz or extended tubular form when constructed of hydrophobic material such as PFA Teflon. The primary condenser has a double bend, with an external threaded drain port at the bottom of the first bend. The end of the second bend faces downward and is connected together by a ball joint or compression fitting or by any other means to a secondary condenser, which is a series of cooling and warming loops.

As the heated aerosol and solvent vapor stream exit the oven, the temperature of the stream begins to drop, reducing the solvent dew point, causing solvent vapors to condense in the primary condenser. Part of the solvent vapor condenses on the inner wall of the condensation loop and flows out or is pumped out of the drain port to waste.

Narrow round tubular condensers made from hydrophobic material such as Teflon PFA will be partially blocked by large droplets of liquid condensate when aqueous samples are analyzed. Various proportions of the analyte aerosol stream will impinge on the liquid condensate and be lost to the measurement process. In addition, hydrophobic tubes do not drain well because liquid condensate adheres non-uniformly to the inner surface of the tubing. When the droplets grow large enough, they will periodically fall under the force of gravity to the drain system. The problem of partial blockage of sample aerosol flow may be solved by using a tube with sufficiently large inner diameter so that condensate droplets will not obstruct the flow of analyte aerosol particles. However, use of larger round tubes results in poor thermal conductivity and poor desolvation. In addition, the larger tube will result in an even higher surface area that will hold solvent condensate droplets in a non-uniform pattern. When the solvent condenser is constructed of hydrophobic materials resistant to hydrofluoric acid with an extended, elliptical, or channelized shape that prevents the aerosol from impacting on a surface or being lost and causing analyte contained therein from being removed from the sample aerosol stream.

The secondary condenser described above is a series of substantially tubular tubes that alternatively cool and warm the aerosol. The three bottom loops fit into three channels of a thermoelectrically cooled metal block. The temperature of the loops is accurately controlled between −5° C. and +20° C. Each of the three bottom loops is fitted with a threaded drain fitting to allow removal of condensed solvent that passes to waste through a length of Teflon tubing leading to a pump system.

When the secondary condenser is constructed of hydrophobic material, such as PFA Teflon, the shape is extended or elongated. This way a Teflon PFA condenser system imparts resistance to HF, will provide proper drainage and stability. The system of the second embodiment utilizes three internal curved surfaces and two straight internal walls to retain thermal transfer properties of round tubular (e.g., quartz) condenser systems, but will allow uniform drainage of condensate away from the sample aerosol flow path. The curved surfaces promote uniform drainage of condensate to the drain which is centrally located within the condenser unit.

As the aerosol stream exits the secondary condenser, it is heated toward an ambient temperature, preventing condensation from any remaining solvent. The exit port connects directly to the injector of the ICP torch, allowing efficient transport of analyte to the ICP for chemical analysis.

Thus it can be seen that the invention accomplishes at least all of its stated objectives.

We claim:

1. A system for use in conditioning a sample for introduction into a sample analysis system, comprising:
   a housing having an upper end, a lower end and an interior;
   a heated cyclonic spray chamber having an inlet and an outlet;
   said inlet of said cyclonic spray chamber being in communication with the sample to be conditioned;
   a desolvation system having an inlet and an outlet;
   said inlet of said desolvation system being in communication with said outlet of said cyclonic spray chamber;
   said outlet of said desolvation system being in communication with the inlet of the sample analysis system;
   said desolvation system comprising a plurality of series connected condenser and revaporization loops.

2. The system of claim 1 wherein said cyclonic spray chamber has a single inlet and a single outlet.

3. The system of claim 1 wherein said cyclonic spray chamber has an upper end, a lower end, and a side wall portion, said inlet being formed in said side wall portion of said cyclonic spray chamber, said outlet being formed in said lower end of said cyclonic spray chamber.

4. The system of claim 1 wherein said cyclonic spray chamber is comprised of a hydrofluoric acid resistant material.

5. The system of claim 1 wherein said cyclonic spray chamber has an inside diameter of approximately 60 mm to 150 mm.

6. The system of claim 1 wherein heat is substantially evenly applied to all surfaces of said cyclonic spray chamber.

7. The system of claim 6 wherein the temperature of the surfaces of said cyclonic spray chamber are heated to 110° C. to 100° C. higher than the boiling point of the solution being analyzed.

8. The system of claim 1 wherein said heated cyclonic spray chamber is heated by a heating mechanism which is not electrically insulating.

9. The system of claim 8 wherein a layer of heated fluid is positioned between said cyclonic spray chamber and said heating mechanism.

10. The system of claim 1 wherein said cyclonic spray chamber is substantially enclosed within a heat conductive material.

11. The system of claim 10 wherein said heat conductive material comprises an aluminum material.

12. The system of claim 1 wherein the sample analysis system comprises an Inductively Coupled Plasma Mass Spectrometer.

13. The system of claim 1 wherein the sample analysis system comprises an Inductively Coupled Plasma Atomic Emission Spectrometer.

14. The system of claim 1 wherein said cyclonic spray chamber is of one-piece construction.

15. The system of claim 1 wherein said outlet of said desolvation system is directly coupled to the inlet of the sample analysis system.

16. The system of claim 1 wherein at least some of said condenser loops are cooled.

17. The system of claim 1 wherein said revaporization loops are subjected to ambient temperatures within said housing.

18. The system of claim 1 wherein each of said condenser and revaporization loops have a generally tubular-shaped cross section.

19. The system of claim 1 wherein said condenser and revaporization loops have a generally tubular-shaped cross section.

20. The system of claim 1 wherein said desolvation system is comprised of a material which is resistant to hydrofluoric acid.

21. The system of claim 1 wherein said desolvation system is comprised of a hydrophobic material.

22. The system of claim 1 wherein said desolvation system is comprised of a Teflon PFA material.

23. The system of claim 20 wherein each of said condenser loops comprises a hollow block member having a front wall, a back wall, end walls, a bottom wall, and an open upper end which is closed by a cover having an inlet opening and an outlet opening formed ther ein.

24. The system of claim 23 wherein said end walls are generally U-shaped in cross section.

25. The system of claim 23 wherein said bottom wall is generally U-shaped in cross section.

26. The system of claim 24 wherein said bottom wall is generally U-shaped in cross section.

27. The system of claim 23 wherein at least some of said condenser loops are coupled to cause the sample passing therethrough to be condensed.

28. The system of claim 27 wherein said revaporization loops are exposed to ambient air within said housing to cause the revaporization of the sample passing therethrough.

29. The system of claim 24 wherein said inlet opening is formed in said cover so as to be positioned adjacent one of said end walls of said hollow block member and wherein said outlet opening is formed in said cover so as to be positioned adjacent the other of said end walls.

30. The system of claim 23 wherein said cover is selectively removably mounted onto said block member.

31. The system of claim 29 wherein a tubular loop member extends between the outlet opening of one block member cover to the inlet opening of an adjacent block member to form said revaporization loop.

* * * * *